United States Patent [19]
Kost et al.

[11] Patent Number: 5,554,841
[45] Date of Patent: Sep. 10, 1996

[54] ARTICLE MARKER AND DECODING METHOD

[75] Inventors: Karen L. Kost; William J. Fry; Timothy Lock, all of Ann Arbor; Michael S. Davis, South Lyon, all of Mich.

[73] Assignee: Lynn Ltd., Ann Arbor, Mich.

[21] Appl. No.: 203,546

[22] Filed: Mar. 1, 1994

[51] Int. Cl.⁶ .............................. G06K 7/10; G06K 19/6
[52] U.S. Cl. ........................................ 235/464; 235/494
[58] Field of Search .................... 235/494, 464, 235/470, 471, 454, 380, 462

[56] References Cited

U.S. PATENT DOCUMENTS

| | | | |
|---|---|---|---|
| 3,418,456 | 12/1968 | Hamisch et al. | 235/61.11 |
| 3,636,317 | 1/1972 | Torrey | 235/494 |
| 3,643,068 | 2/1972 | Mohan et al. | 235/464 |
| 3,752,961 | 8/1973 | Torrey | 235/61.11 |
| 3,808,405 | 4/1974 | Johnson et al. | 235/61.12 |
| 3,916,160 | 10/1975 | Russo et al. | 235/61.11 |
| 4,059,225 | 11/1977 | Maddox | 235/437 |
| 4,874,936 | 10/1989 | Chandler et al. | 235/494 |
| 4,896,029 | 1/1990 | Chandle et al. | 235/494 |
| 4,924,078 | 5/1990 | Sant' Anselmo et al. | 235/494 |
| 4,939,354 | 7/1990 | Priddy et al. | 235/456 |
| 5,053,609 | 10/1991 | Priddy et al. | 235/436 |
| 5,124,538 | 6/1992 | Lapinski et al. | 235/467 |
| 5,130,795 | 7/1992 | Rusche et al. | 358/108 |
| 5,153,418 | 10/1992 | Batterman et al. | 235/494 |
| 5,374,813 | 12/1994 | Shipp | 235/375 |

FOREIGN PATENT DOCUMENTS

| | | | |
|---|---|---|---|
| 0240688 | 10/1988 | Japan | 235/494 |
| 0075091 | 3/1990 | Japan | 235/494 |
| 0071162 | 6/1990 | WIPO | 235/494 |

*Primary Examiner*—Donald T. Hajec
*Assistant Examiner*—Thien Minh Le
*Attorney, Agent, or Firm*—Gifford, Krass, Groh, Sprinkle, Patmore, Anderson & Citkowski

[57] ABSTRACT

A graphical symbol encoding a numerical value may be accurately read even when placed on a non-planar surface. The marker is imaged with an inventive apparatus and analyzed using an inventive method which translates the graphical image into a unique number for article identification purposes. The marker in its preferred embodiment includes an outer ring having a continuous perimeter in one or more concentric data tracks disposed within this outer ring. A timing track is used to determine angular relationships about the center of the marker. Distances between points associated with the outer ring in a particular data track are used in conjunction with these angular relationships to locate a digitally encoded visual pattern associated with a particular data track, this pattern being used to store at least a portion of a numerical code used to identify each marker-bearing article.

22 Claims, 4 Drawing Sheets

ARTICLE MARKER AND DECODING METHOD

FIELD OF THE INVENTION

This invention relates generally to computer-readable symbology, and, in particular, to an encoded marker that may be accurately read from an article even if placed on a non-planar surface.

BACKGROUND OF THE INVENTION

It is now common to track an inventory of various types of articles using computer-readable encoded symbology. Universal product codes are now common on an increasing number of consumer items, and packages and mail are sorted using computer-readable bar codes with increasing frequency.

In many applications, it is desirable to increase the amount of information that may be carried by an encoded marker. This has led to the development of two-dimensional bar codes. By encoding information in two dimensions, such codes may dramatically increase the amount of information-carrying capacity, but present trade-offs which affect accurate reading. Being two-dimensional, these higher capacity codes demand accurate scanning and decoding along two axes, which places further demands on the reading environment, including the types of surfaces upon which such symbology may be placed, lighting conditions, and the amount of processing time required to obtain an accurate reading.

Ideally, the decoding of such two-dimensional markers is preferably performed from a flat surface. In this way, the scanner or reading mechanism if held stable for a long enough period of time, may derive accurate information in a short time, since distortion of the encoded imagery need not be taken into account. However, there are a large class of articles which contain few, if any, flat surfaces, including surgical and scientific instruments, machined parts, tools, ammunition, keys, certain micro electronic components and so forth. In such applications, a new information-bearing marker is required, one that may be read from such articles, even in the event that the marker is placed on a curved or non-planar surface associated with the marker.

SUMMARY OF THE INVENTION

The present invention provides a marker encoding a numerical value which may be read from even a non-planar surface. The marker is imaged with an inventive apparatus and analyzed with inventive steps which translate the graphical image of the marker into a unique number, which may be referenced for various tracking and inventory management purposes.

The marker in its preferred embodiment includes an outer ring having a continuous perimeter and one or more concentric data tracks disposed within this outer ring. A timing track is used for the determination of angular relationships about the center of the marker. Distances between points associated with the outer ring and a particular data track are used in conjunction with these angular relationships to locate a digitally encoded visual pattern associated with a particular data track, this pattern being used to store at least a portion of a numerical code used to identify each marker-bearing article.

The marker is preferably substantially circular in shape, as are the data tracks, however, when etched or otherwise disposed on a curved or non-planar surface, aspects of the marker, including the data tracks, may appear in distorted form upon imaging. However, since the present invention uses ratios or percentages of distances and angular relationships as opposed to absolute values, the marker pattern and decoding methods of the invention are such that accurate reading and decoding is possible even in the case of highly distorted marker images, thus facilitating a reliable article tracking system.

The preferred method of decoding a marker comprises the steps of locating the marker within an image field, finding points along the perimeter of the marker, analyzing the points along the perimeter in order to determine the shape of the marker, and using the outer shape to find a data track within the area defined by the perimeter of the marker. A timing track is also located to determine angular relationships relative to the center of the marker, and these angular relationships in conjunction with distances relative to the outer shape are then used to find and decode the bit pattern associated with a data track disposed within the outer perimeter of the marker. In the preferred embodiment, three data tracks are used to store 8, 16, and 24 bits of information, with certain of these bits being dedicated to error detection and correction to further ensure an accurate reading.

DETAILED DESCRIPTION OF THE EMBODIMENTS

The marker is imaged by a reader apparatus formed in accordance with this invention and analyzed using an inventive method which translates the marker into a unique number used for identification purposes. The numerical code assigned to a particular article may, for example, be used as a pointer into a data base, enabling the article to be identified as to its type and other characteristics.

As other examples outside the medical profession, the invention may be used in conjunction with identifying small machine or electronic components for commercial, industrial or military purposes, or for the marking of controlled articles, such as weaponry, ammunition, and so forth.

Figure 1:
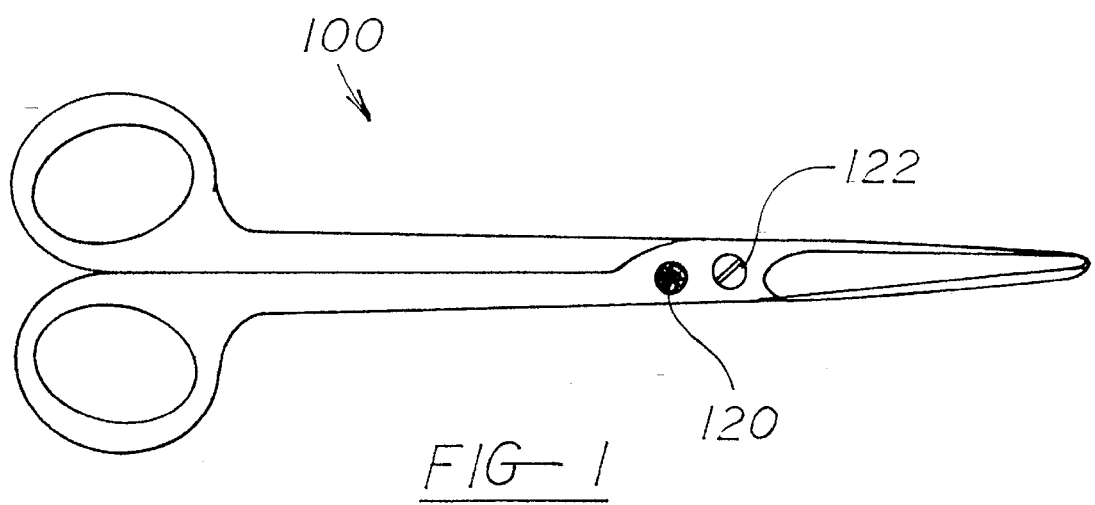
FIG. 1 is a drawing of an article including a marker representative of that used according to the present invention.

FIG. 1 shows just one use of the present invention, in this case a pair of common straight Mayo-Hegar scissors 100 of the type used to remove wound dressings in hospital situations. As is the case with many such instruments, the scissors 100 are made of a hard and relatively inert alloy or composition such as stainless steel which contains few, if any, flat surfaces upon which to form identifying indicia. However, with the present invention, an information-bearing marker or target 120 may be etched into the instrument itself in a permanent manner, virtually on any surface large enough to contain this indicia. In FIG. 1, for example, this marker is shown on one side slightly down the handle and away from the fastener 122 which holds the two halves of the scissors together, though numerous other locations are possible, as is the possibility of using more than one marker simultaneously on the same instrument or article.

Figure 2:
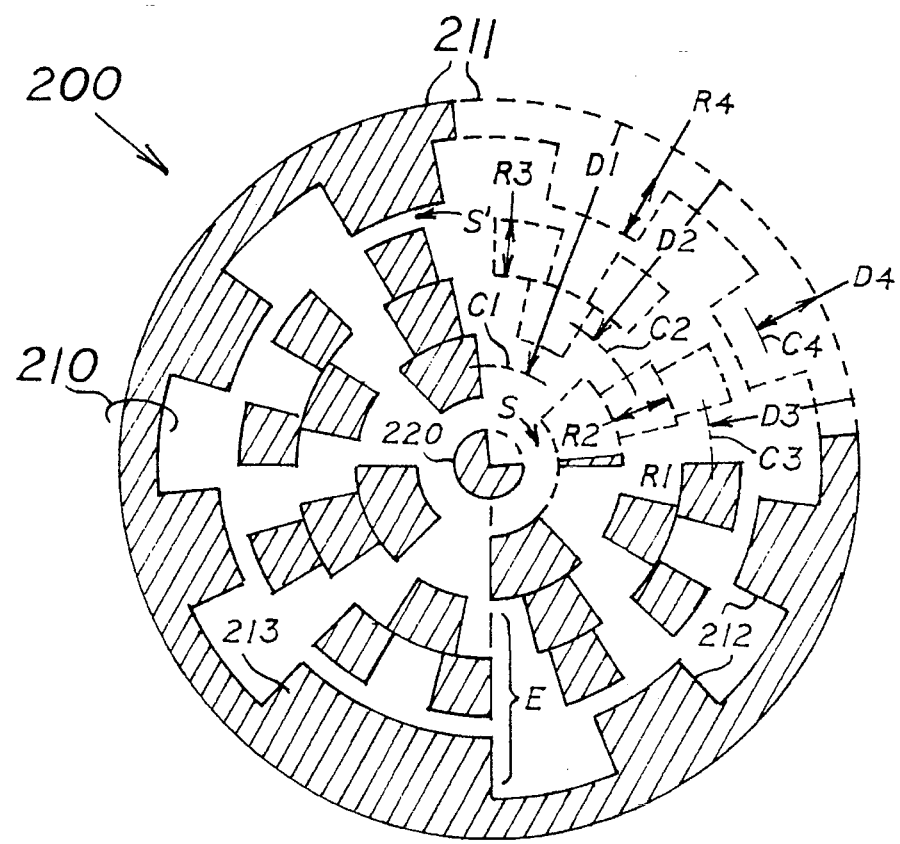
FIG. 2 is a representation of a circular marker comprising a unique alternating bit pattern used to introduce features associated therewith.

Since the details of marker 120 are not apparent in FIG. 1, FIG. 2 will be used to introduce some of the concepts and dimensions associated therewith. A portion of the marker is shown with broken lines for clarification purposes only. In its preferred, undistorted form, the marker 200 includes a generally circular outer ring 210 having a continuous perimeter 211 used as a locator. Extending inwardly from this ring 210 are plurality of timing segments 212, including a uniquely wider starting segment 213, which also serves as a locator, the function of which will be described in more detail below. Segments 212 and 213 reside within a timing track defined by R4.

In the embodiment shown in FIG. 2, there are also three information-containing concentric bands or rings R1, R2 and R3, which are separated from an inner dot 220 by space S, with a second space, S1, being used to separate patterns contained in ring R3 from segments 212 and 213. The exact geometry shown in FIG. 2 is not required to be in keeping with the present invention, however. For example, rings R1, R2 and R3 need not be adjoining as shown, and spaces S and S1 may be adjusted or eliminated. Also, though three rings are shown, more or fewer may be used, depending upon the circumstances, including the size of the required database, and spaces may be introduced between data rings or between bit patterns within a ring. Center dot 220, though preferred for location purposes, is also in fact optional, as are the precise number and shape of segments 212 and 213.

Continuing the reference to FIG. 2, data are digitally encoded in the various rings which may be in the form of a visually readable pattern, such as etched and non-etched regions, which result in patterns light and dark areas. For example, in R1, there are eight sectors, each which may be etched or non-etched, thereby affording the capacity for eight bits of information, or numbers up to 256. The patterns of rings R1, R2 and R3 in FIG. 2 depict a unique hypothetical situation involving alternating bits. This is done only to help illustrate the relative positioning and size of each potential data field. In practice, the pattern associated with each marked instrument will be unique and therefore representative of a different encoded numerical value.

Ring R2 preferably includes sixteen sectors, enabling 65,536 unique codes, and ring R3 includes twenty-four sectors, representing 16,777,216 codes. Thus, adding the potential unique markings available with just three rings as shown in FIG. 2, 232 different articles or instruments may be marked with a unique identifying number, and in the event that further rings are added, the potential number of unique codes is vastly increased.

In order to read an encoded pattern associated with a particular data track, the radial displacement of a data track relative to points associated with the outer ring is used in conjunction with angular displacement along the ring relative to a point or points associated with the starting segment 213. As such, the distance from the outer perimeter 211 to the center line of each ring is important, since this distance will be followed in order to locate the digital data stored in that ring. For example, in FIG. 2, distance D1 represents the distance from the outer perimeter 211 to the centerline C1 of data ring R1, distance D2 represents the distance from outer perimeter 211 to the centerline C2 of ring R2, and distance D3 represents the distance from the outer perimeter to the centerline C3 of data ring R3. Additionally, distance D4 represents the distance from the outer perimeter to the centerline C4 of a ring R4 which includes the segments 212 and 213.

Although the distances D1 through D4 are measured radially inwardly with respect to the outer perimeter 211, as will become apparent from the discussion below, other distances may be used, including other points associated with the outer ring 210 or, alternatively, distances radially inward from the center point 220.

Figure 3A:
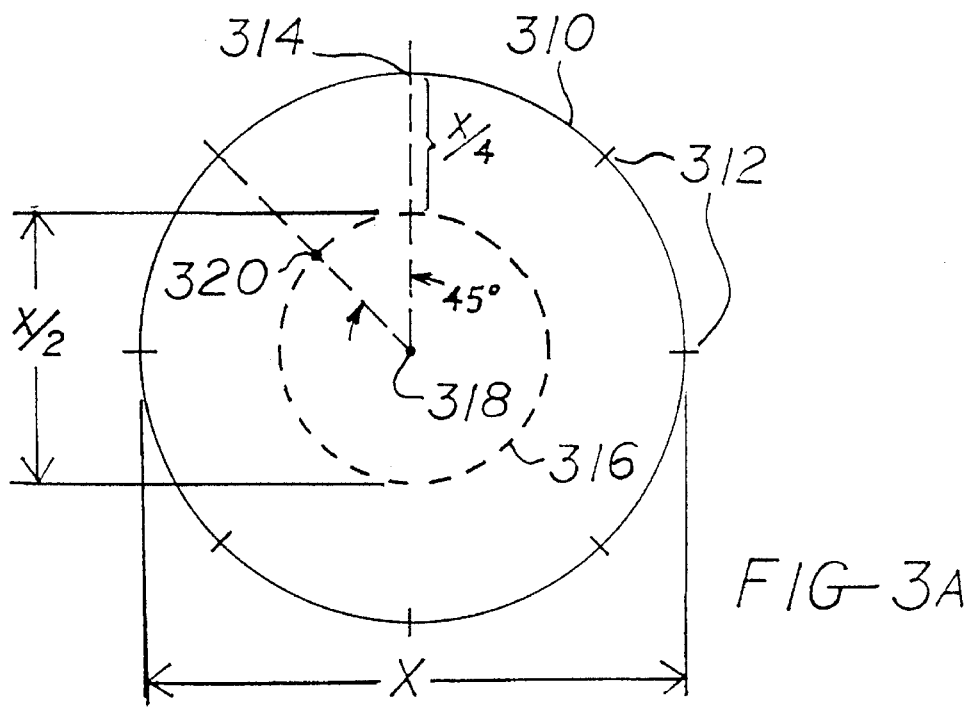
FIG. 3A is a skeletal diagram of a hypothetical circular marker having one data track and one point to be decoded.
Figure 3B:
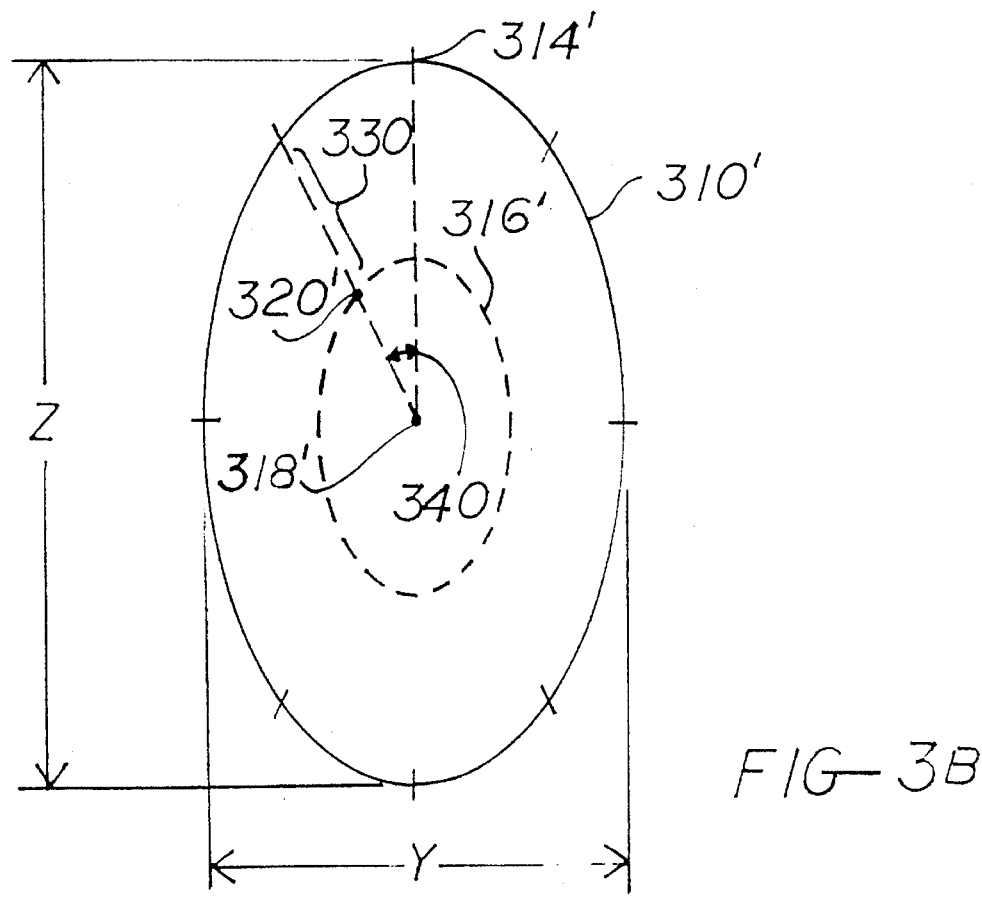
FIG. 3B is a highly distorted version of the marker of FIG. 3A, used to illustrate how ratios may be used in lieu of absolute values yet obtain an accurate reading of an encoded pattern.

FIG. 3A shows a non-distorted circular representation of a highly schematic version of a marker which will be used to show how a particular data point may be found by practicing the present invention, even if the marker becomes highly distorted, as shown in FIG. 3B. It must be borne in mind that FIGS. 3A and 3B are used only to show how ratioing and percentages are used in the present invention to ensure an accurate reading even on a curved or non-planar surface, and that many of the features of the skeletanized version of the marker in FIGS. 3A and 3B are left out, including the timing track, multiple data tracks, and the center dot. Nevertheless, these diagrams are useful for the broad concepts which will now be explained.

Referring to FIG. 3A, there is shown a marker having a substantially circular outer perimeter 310, and a plurality of timing marks 312 about this perimeter including a starting mark 314. This diagram includes one data track 316 substantially circular in shape, and both the outer perimeter 310 and the data track 316 are concentric about a center point 318. The outer shape is given a diameter of X, with the diameter of the data track 316 being X/2. Assume that a single bit of a data is to be stored at a point 320 along data track 316 at an angle of 45° relative to the start mark 314. As such, this region may be easily located, given the known angle of 45° and the fact that the distance from the outer ring 310 as measured radially inwardly therefrom, must be X/4. In this case, a data point may be easily located in the two-dimensional region defined by the marker overall, using radial displacement in one dimension and angular displacement in another. If the marker were to remain perfectly circular, an absolute value could be used to locate a data track. In other words, given a value of X=2, the distance from the outer perimeter 310 and the data track 316 will always be 1 regardless of the angular displacement.

The situation of FIG. 3A changes dramatically if the marker is imaged from a none-planar surface, resulting in an oval-shaped outer perimeter 310' and a similarly shaped oval data track 316'. The width Y of the oval is no longer equal to X, nor is the height Z. Furthermore, the distance as measured radially inward from the outer perimeter 310' to the data track 316' varies as a function of angular displacement about the center point 318'. Now the distance as measured radially inwardly 330 to the point 320' to be read is no longer equal to X/4, nor is the angle 340 equal to 45°. As such, for such a highly distorted version of the marker, the use of absolute values is out of the question.

Therefore, the present invention instead uses ratios or percentages of distances measured across the marker or between the outer perimeter of the marker and its center point, in conjunction with radial displacement around the center point 318. For example, instead of storing the fact that data track 316 is equal to an exact distance from the outer perimeter, what is stored is the fact that this distance is 25 percent of the distance across the entire marker and through the center point 318 or, alternatively, as 50 percent of the distance between the outter perimeter 310' and the center point 318'. Similarly, in terms of angular displacement, instead of storing the fact that an angle of 45° should be used to locate the data point, the system instead uses a new angle, using timing marks such as mark 340. By drawing a line from this mark and into the center point 318', it is now known that data should be read in the vicinity of the intersection of this segment and the data track 316'.

Figure 4:
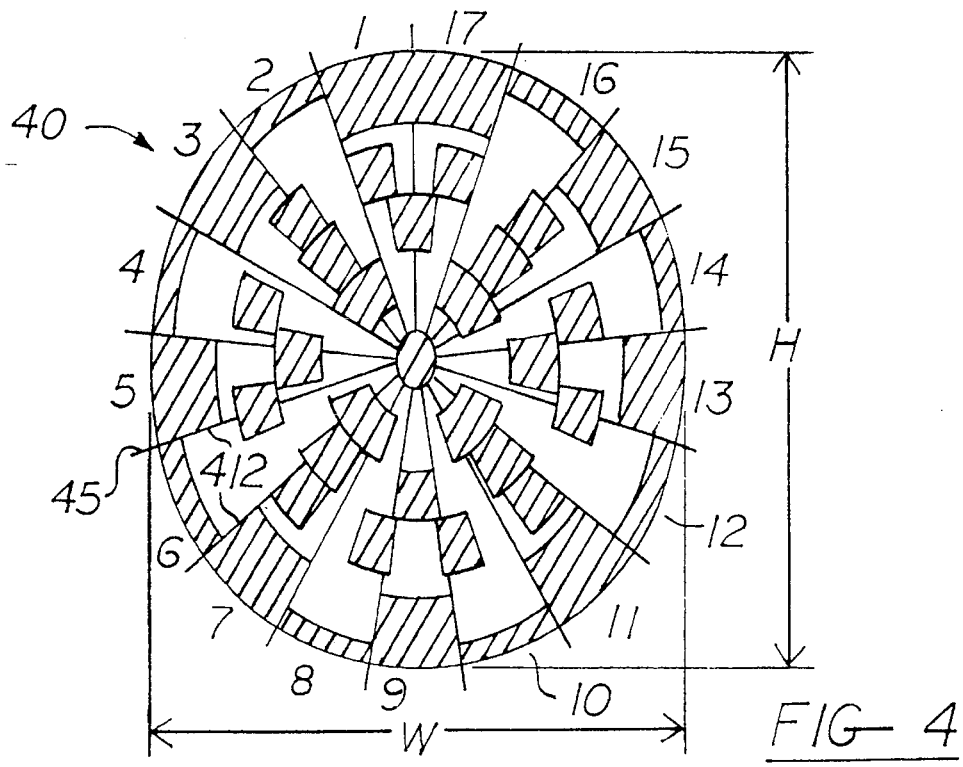
FIG. 4 illustrates how the marker of FIG. 2 may become distorted through placement on a non-planar surface.

FIG. 4 shows how the marker of FIG. 2 is actually distorted upon reading from a non-planar or curved surface. With the discussion concerning FIGS. 3A and 3B in mind, it should now be understood that by using distances across this distorted marker and angular displacements relative to the edges of the timing segments 412, the data patterns associated with the three timing rings may now be found and accurately read. Even though the situation is now considerably more complicated than that shown in FIGS. 3A and 3B, the same principles introduced therein may still be utilized successfully in the case of FIG. 4.

A more detailed description of the actual steps used in a preferred embodiment of the present invention will now be described with reference to the flowchart shown in FIG. 5. Reference will also be made to the distances and definitions made with regard to an idealized circular marker shown in FIG. 2. The apparatus used will be discussed with reference to FIG. 6. Having adjusted gain and level on an apparatus used to digitize the area of the article including the marker at step 1, the image is snapped at step 2. In this application, "snapping" refers to the actual conversion of the light received from the marker and its surrounding environment into electrical signal representative of the light received.

As shown in step 3, high frequency projections along the X and Y axis are computed and, based upon the frequency of occurrence two-dimensional objects, a window region of interest is created at step 4. In step 5, a histogram of the window region of interest determined in step 4 is computed and, based upon the shape of this histogram, gain and level of the digitization apparatus may be reset accordingly at step 6. It should be noted that steps 1–6 are in fact optional, and may be repeated so as to gather image data with the highest resolution and contrast.

If steps 1–6 have been performed or are not required, the image is snapped at step 7, and the window data copied from the scanning apparatus into random access memory for further computation. At step 9, an adaptive threshold is created for the window image to enhance accuracy, and at step 10 the window data and adapted threshold of the image are used to create a run length encoded version of the marker image. Run length encoding is well known in the art of computer graphics, and may be referenced, for example, in the text, *Computer Graphics Principles and Practice* by Foley and vanDam, Addison Wesley Publishing Company.

Subsequent to run length encoding, a connected components analysis is performed at step 11 to determine which pixels are connected to their nearest neighbors. The preferred method uses an 8-way connectivity wherein any neighbor is connected to another if both contain the same digital data and are horizontal, vertical or diagonally adjacent relative to one another. At this stage, the system is primarily attempting to identify the outer peripheral band 210 shown in FIG. 2, to first ascertain whether the connected components do, in fact, represent a marker.

For each mass of connected pixels in the field of view, the system computes component moments at step 12 representative of two-dimensional area, position and eccentricity. Ignoring details within the center of the mass initially, the system searches to determine if a particular mass has a proper area and eccentricity within a particular tolerance so as to be a candidate marker. Candidates may be filtered for the location of the center dot at step 13 using values of area, center of mass, and so forth. The center dot is not necessary to the present method, since the image of the entire marker may be normalized from edge to edge. Use of the center dot therefore essentially cuts the normalization error roughly in half, which may be advantageous in problematic situations.

At step 14, the computed component moments are filtered to determine the outer ring of the marker using area, position and eccentricity values. Once the outer ring has been determined, a radial distance table is created at step 15 from the run length encoded data representative of the ring. Once the radial distance table has been constructed, the location of the various data tracks may be determined, as explained with reference to FIGS. 3A and 3B.

Knowledge of the distorted shape of each data track is insufficient, however, since the data must also be located with respect to its position along a particular track. To ensure that the data are located along even those tracks distorted from circularity, the system further examines the positioning of segments 212 and start segment 213 to adjust for angular distortion, and build an angle table at step 16 using data from steps 8 and 9. For example, in FIG. 2, there are shown seven segments 212 and one segment 213 which essentially occupies the space of two segments 212 side by side. Between each timing segment 212 and the start segment 213 there are eight spaces of equal size to segments 212. The edges associated with each of the segments 212 with the addition of a line drawn through the center of segment 213, results in seventeen pie-shaped segments, which are numbered 1 through 17 in FIG. 4. If the marker were ideally circular in shape, this would result in seventeen equal sections equalling 360°, each comprising an angle of approximately 21.18 degrees. However, should the ideal circular shape be distorted from being projected onto a curved or non-planar surface, these angles will change, but if the degree of change is known it may be still used to accurately locate data. For example, in FIG. 4, with width W being smaller than height H, the angles associated with segments such as 1, 17, 8, 9 and 10 will be slightly less than angles associated with segments 4, 5, 13 and 14.

Making use of the adjustments just discussed, in operation, having located the marker overall, the system uses the distortion from circularity in the form of radial distance ratios to determine the approximate distortion of all otherwise circular timing and data tracks. Beginning at the outermost edge of the marker, the system first locates the centerline C4 associated with the timing track R4 containing segments 212 and 213 which, as just discussed, may be non-circular in form. The system analyzes this path, taking into account all edges associated with segments 212 and 213, and the distances involved therewith. Since the distances between these segments would otherwise be equal in the case of a perfectly circular marker, in the event that they are not equal, the system takes this into account to calculate the angles formed between the interfaces to these segments as measured radially outwardly from a center of mass within the overall marker.

Having found these angles, the system then begins at the edge 45 shown in FIG. 4 and proceeds to the centerline path C1 associated with the ring R1 and travels along this path, adjusted in accordance with the radial distance table, and looks for encoded digital data. For example, using R1, the system travels along the centerline to determine if any of the potential 8 available pattern spaces along this data track is encoded. When it is finished examining this path, having stored the data encoded therein, the system proceeds out to the centerline C2 associated with ring R2, again using degree of distortion and radial angle values to locate and decode the sixteen bits of information stored, then proceeds out to the centerline C3 associated with R3 and decodes those eight bits. Although the read sequence of the bits is from the inner ring to the outer ring in a counter-clockwise manner, this is not important to me invention since inner to outer, clockwise or counter-clockwise are all equally valid conventions for the ordering of the data.

Figure 5:
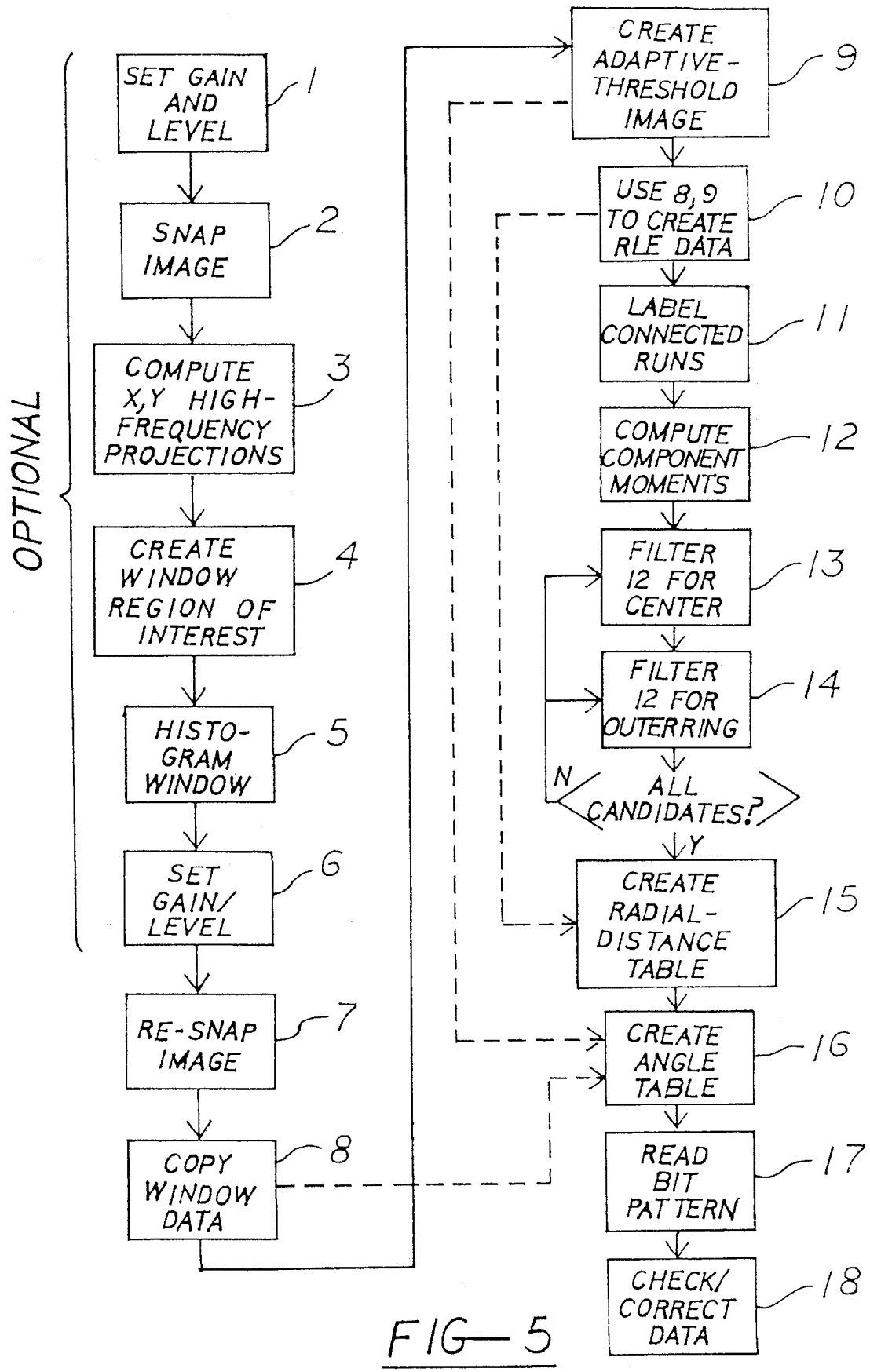
FIG. 5 is a flow diagram of steps taken during a preferred reading process according to the present invention, some of these steps being optional.

Having determined the digitally encoded data represented by step 17 in FIG. 5, step 18 is preferably used to check and the correct the data bits in accordance with error correction and detection. As mentioned, though the system with three rings facilitates 48 digital bits of information, certain of the bits are advantageously allocated to error detection and correction. For example, of the 48 total bits represented by the 3 rings, 32 are preferably used for data with the remaining 16 being used for error correction and detection such that four of the data bits may be decoded incorrectly but using the error correction bits may be reconstructed to facilitate an accurate reading.

Figure 6:
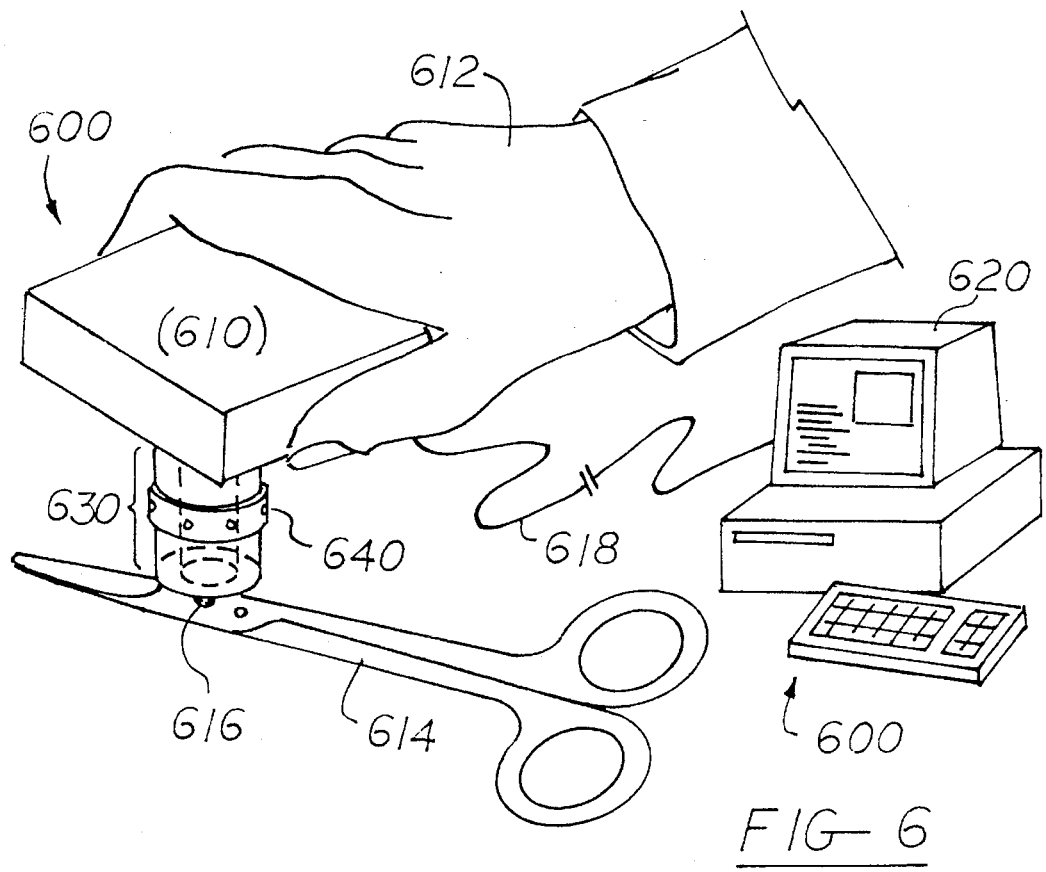
FIG. 6 shows an apparatus for reading the code on the surface of an article.

Now making reference to FIG. 6, there is shown an embodiment of the apparatus aspect of the present invention indicated generally at 600, including a hand-held scanning device 610 in use by an operator 612. As shown in the figure, a surgical implement 614, such as that originally depicted in FIG. 1, is being scanned by the implement 610 to read marker 616 previously etched on the implement and encoding a unique numerical value. The electronics within unit 610 includes a video input device, preferably a high resolution charge-coupled device (CCD) camera, which outputs a video signal along line 618 to computer 620, which performs the steps mentioned above to decode the marker and, based upon the numerical value decoded therefrom, brings up one or more records on the screen of computer 620 which represent information pertaining to the implement 614.

In order to enhance signal to noise, a barrel of translucent material 630 is used to gather an image of the marker and deliver it to the CCD within scanner 610. A band of illumination sources 640 is preferably used around the outside of the barrel 630, preferably in the form of infrared light-emitting diodes (LEDs), though any other type of illumination source disposed peripherally around tube 630 or otherwise, may be used to improve illumination. It has been found, however, that due to the fact that existing CCD imagers are very sensitive in the infrared region, such infrared LEDs are particularly advantageous for illumination purposes.

Barrel 630, which preferably has side walls which taper from a larger opening at its distal end to a slightly smaller opening at its proximal end in the vicinity of the image sensor, also helps to reject stray images which might tend to compete with that of the marker 616. Although the use of barrel 630 and illumination source 640 are optional, it has further been determined that due to the specular surface present on many of the articles which might take advantage of the invention, barrel 630 and ring of illumination 640 help to remove spurious images, such as reflections of the CCD image sensor itself off of the surface bearing the encoded marker. Other modifications of the present invention are possible in light of the above description which should not be deemed as limiting the invention beyond those limitations contained in the claims which follow.

We claim:

1. A marker digitally encoding a numerical value, comprising:

a perimeter having a predetermined shape;

a center;

a plurality of references, spaced apart around the perimeter to determine angular displacement about the center;

at least one concentric data track disposed within the perimeter, the shape of the track being substantially similar to that of the perimeter;

a digitally encoded bit pattern associated with the data track, the location of a particular bit within the pattern being determinable as a function of angular displacement and distance as measured radially inwardly from the closest point associated with the perimeter.

2. The marker of claim 1 wherein the perimeter and data track are substantially circular in shape.

3. The marker of claim 2 wherein the distance as measured radially inwardly from the perimeter represents the diameter of the circle.

4. The marker of claim 2 wherein the distance as measured radially inwardly from the perimeter represents the radius of the circle.

5. The marker of claim 1, including bits dedicated to error detection and correction.

6. An article tracking system, comprising:

means to apply a marker according to claim 1 on an article;

a programmed computer including means to input an image of the marker on the article; and software resident on the computer to process the image of the marker and decode its numerical value.

7. The system of claim 6, further including means to uniformly illuminate the marker on the article to improve imaging accuracy.

8. An article tracking method, comprising the steps of:

marking an article with a pattern storing a unique number in the form of digital bits disposed along at least one data track contained within a perimeter, the location of a particular bit in the track being defined by the steps of:

a. determining angular displacement along the data track followed by, b. measuring the distance radially inwardly with respect to the closest region of the perimeter of the marker.

9. The method of claim 8, further including the steps of:

finding the center of the marker; and calculating the distance between the points along the perimeter of the marker in conjunction with the center of the marker to determine the outer shape of the marker.

10. The method of claim 9, wherein the step of finding the center of the marker includes:

imaging visual indicia indicative of the center of the marker.

11. The method of claim 8, wherein:

the step of using the outer shape to find a data track within the area defined by the perimeter of the marker includes finding a timing track, the step of reading the timing track includes finding angular relationships between points along the timing track and the center of the marker, and further including the step of:

using the angular relationships in conjunction with the outer shape to find and read a data track other than the timing track.

12. The method of claim 8, further including the steps of:

storing data representative of a predetermined marker shape;

comparing points found along the perimeter of the located marker with the data representative of the predetermined marker shape to determine one of more adjustment factors; and using an adjustment factor to find a data track within the area defined by the perimeter of the located marker.

13. The article tracking system of claim 6, the article being a surgical instrument.

14. The method of claim 8, wherein the step of marking an article includes the step of marking a surgical instrument.

15. A marker digitally encoding a numerical value, comprising:

a perimeter having a predetermined shape;

a center;

at least one reference to determine angular displacement about the center; and at least one data track disposed within the perimeter, the data track including a bit pattern digitally encoding a numerical value, the location of a particular bit within the pattern being determinable as a function of angular displacement and a ratio of distance as measured across the marker.

16. The marker of claim 15, the shape of the data track being in geometric conformance with that of the perimeter.

17. The marker of claim 16 wherein the perimeter and data track are substantially circular in shape.

18. The marker of claim 15, including a plurality of concentric data tracks.

19. A marker digitally encoding a numerical value, comprising:

a perimeter having a predetermined shape;

a center;

at least one reference to determine angular displacement about the center;

at least one data track disposed within the perimeter, the data track including a bit pattern digitally encoding a numerical value, the location of a particular bit within the pattern being determinable as a function of angular displacement and a ratio of distance as measured between the center and perimeter of the marker.

20. The marker of claim 19, the shape of the data track being in geometric conformance with that of the perimeter.

21. The marker of claim 20 wherein the perimeter and data track are substantially circular in shape.

22. The marker of claim 20, including a plurality of concentric data tracks.

* * * * *